United States Patent
Doherty et al.

(10) Patent No.: US 8,372,447 B2
(45) Date of Patent: Feb. 12, 2013

(54) COMPOSITIONS AND METHODS FOR PROMOTING WEIGHT LOSS AND INCREASING ENERGY

(75) Inventors: John Doherty, Oakville (CA); Phil Apong, Oakville (CA); James Akrong, Oakville (CA); Shawn Shirazi, Oakville (CA)

(73) Assignee: Northern Innovations and Formulations Corp., Ontario (CA)

( * ) Notice: Subject to any disclaimer, the term of this patent is extended or adjusted under 35 U.S.C. 154(b) by 184 days.

(21) Appl. No.: 12/849,076

(22) Filed: Aug. 3, 2010

(65) Prior Publication Data

US 2012/0034323 A1 Feb. 9, 2012

(51) Int. Cl.
*A61K 36/515* (2006.01)

(52) U.S. Cl. ........ 424/725; 424/732; 424/757; 424/728; 424/767; 424/764; 424/687; 424/747; 424/750; 544/274; 514/474; 562/570; 562/563

(58) Field of Classification Search .......... None
See application file for complete search history.

(56) References Cited

FOREIGN PATENT DOCUMENTS

| JP | 2002-101859 A | * | 4/2002 |
| JP | 2004-256476 A | * | 9/2004 |
| JP | 2008-069134 A | * | 3/2008 |

OTHER PUBLICATIONS http://www.benefits-of-honey.com/health-benefits-of-honey.html—accessed May 2012.*
Table of Contents for Clinical Nutrition, vol. 28, No. 2, Apr. 2009.*
Girotti (Planta Med (2005), vol. 71, pp. 1170-1172).*
Aybar, et al., "Hypoglycemic effect of the water extract of *Smallantus sonchifolius* (yacon) leaves in normal and diabetic rats", Journal of Ethnopharmacology, vol. 74 (2001) 125-32.
Genta, et al., "Yacon syrup: Beneficial effects on obesity and insulin resistance in humans", Clinical Nutrition, vol. 28 (2009) 182-7.
Geyer et al., "Effect of Yacon (*Smallanthus sonchifolius*) on Colonic Transit Time in Healthy Volunteers", Digestion, vol. 78, (2008) 30-3.
Kweon, et al., "Identification and Antioxidant Activity of Novel Chlorogenic Acid Derivatives from Bamboo (*Phyllostachys edulis*)", J. Agric. Food Chem., vol. 49 (2001) 4646-55.
Lafay, et al., "Chlorogenic Acid is Absorbed in Its Intact Form in the Stomach of Rats", J Nutr., vol. 136 (2006) 1192-7.
Lafay et al., "Absorption and metabolism of caffeic acid and chlorogenic acid in the small intestine of rats", Br J Nutr., vol. 96 (2006) 1-8.
Marques et al., "Chlorogenic acids and related compounds in medicinal plants and infusions", Food Chemistry, vol. 113 (2009) 1370-76.
Simonovska et al., "Investigation of phenolic acids in yacon (*Smallanthus sonchifolius*) leaves and tubers", Journal of Chromatography A, vol. 1016 (2003) 89-98.
Valentova et al., "*Smallanthus sonchifolius* and *Lepidium meyenii*—prospective Andean crops for the prevention of chronic diseases", Biomed. Papers, vol. 147, No. 2 (2003) 119-30.
Valentova, et al., "Antioxidant activity of extracts from the leaves of *Smallanthus sonchifolius*", Eur J Nutr, vol. 42 (2003) 61-6.
Toriumi, et al., "New Triterpenoids from *Gentiana lutea*", Chem. Pharm. Bull., vol. 51, No. 1 (2003) 89-91.
The Herbal Resource, "Natural Supplements to Gain Weight", accessed May 1, 2012.

\* cited by examiner

*Primary Examiner* — Susan Hoffman
(74) *Attorney, Agent, or Firm* — Fitzpatrick, Cella, Harper & Scinto

(57) ABSTRACT

The present invention relates to compositions comprising plants and extracts of plants with chlorogenic acids and antioxidants and/or caffeine; methods for preparing the same; and methods to promote weight loss through the administration of compositions containing these plants and plant extracts in specific proportions.

20 Claims, No Drawings

COMPOSITIONS AND METHODS FOR PROMOTING WEIGHT LOSS AND INCREASING ENERGY

FIELD OF THE INVENTION

The present invention relates to novel methods and compositions comprising chlorogenic acids for promoting weight loss, for the treatment of obesity, managing weight gain, or maintenance of normal body weight and for increasing energy of an individual participating in a weight loss regimen.

BACKGROUND OF THE INVENTION

Obesity is one of the most common medical disorders and affects about 30-40% of the population of the United States, 10% of which may be severe and morbid. Complications of obesity include insulin resistance, diabetes mellitus (and its complications, including oxidative stress), hypertension, cardiovascular disease, hyperlipidemia, sleep apnea, cancer, pulmonary hypertension, cholecystitis, and osteoarthritis are major reasons for medical intervention. The mortality from obesity is estimated at 300,000 to 400,000 per annum in the United States. The exact etiology of obesity is unknown but occurs when energy intake exceeds energy expenditure.

One main contributing factor in obesity is overeating, which results in an excess of energy being consumed in relation to the amount of energy expended by an individual. The excess energy is then stored largely as fat. An individual's body weight is essentially governed by the net effect of energy consumed versus energy expended. Daily energy expenditure consists of three components: basal metabolic rate, adaptive thermogenesis and physical activity. All of the aforementioned components must be in a balance of energy expenditure in an individual with energy or food intake so that an individual does not gain nor lose body weight. Therefore, for that person to lose body weight from a reduction in adipose tissue, more energy must be expended by the individual than taken into the body.

Losing weight and keeping it off is very difficult for most individuals. Weight gain results when an individual's caloric intake exceeds the number of calories expended as energy. In attempting to lose weight, an individual may utilize a regimen of caloric deficit (i.e. decreasing caloric intake so that calories expended as energy exceed caloric intake). Generally, the result is an adaptive response of a lowered basal (resting) metabolic rate. Caloric deficit can also cause a loss of skeletal muscle. Thus, weight loss or reducing caloric intake results in a lowering of resting energy expenditure and loss of lean body mass. This makes it harder to keep the weight off once the individual has attained his desired weight goal.

When the body encounters an energy deficit in the course of weight-reducing diets, it tends to save energy by reducing thermogenesis. This factor contributes to a failure in sustaining body weight after body weight loss. These circumstances require continually stimulated thermogenesis. After losing weight for a short duration, an individual's weight stabilizes. In order to maintain body weight there is a need to control food intake, stimulate thermogenesis and increase energy levels on an ongoing basis.

Some undesired effects encountered by individuals desiring to loss weight include fatigue, low energy, and a lack of motivation and/or depression.

Another undesired effect of increased accumulation of body fat is an increased oxidative stress through the generation of reactive oxygen species and the downregulation of antioxidative enzymes. This downregulation of antioxidative enzymes can contribute to the pathogenesis of diabetes, hypertension and atherosclerosis. Thus it is desirable to provide an individual means to reduce stored body fat and simultaneously offer protection from reactive oxygen species.

Increased oxidative stress due to increased body fat is thought to be an early contributor to hypertension, coronary heart disease, type 2 diabetes mellitus, stroke and even some forms of cancer and is therefore an attractive target strategy for combating the negative effects of excessive body fat while aiming to reduce the volume of stored body fat in an individual.

With the unprecedented rise in obesity throughout the world, there exists both a need and want from individuals for improved aids, methods and interventions directed to reducing body fat and maintaining lowered levels of body fat, while also supplying beneficial antioxidant activity.

While not necessarily obese, many individuals who are overweight can also suffer from many similar conditions known to be associated with obesity including, among others, poor self-esteem and low self-confidence, poor dietary and exercise habits, lack of energy and anxiety. Many of these individuals would benefit from the prevention or correction some of these conditions if they were able to prevent weight gain and/or maintain a normal body weight.

Therefore, there is a need to provide individuals compositions useful for increasing energy and promoting weight loss, for the treatment of obesity, prevention of weight gain or maintenance of normal body weight and increasing energy.

SUMMARY OF THE INVENTION

The present invention provides for a dietary supplement that provides any one or more of the following benefits: help reduce and control appetite; help control food cravings; help reduce hunger cravings; help induce feeling of fullness (satiety); promote and support weight loss; help reduce body mass index (BMI); help reduce waist and thigh measurements; increase metabolism; increase thermogenesis; and increase energy.

In aspects, the present invention relates to methods and compositions that utilize plants and/or portions thereof containing chlorogenic acids.

According to another aspect of the invention, the dietary supplement further comprises at least one substance for increasing energy.

According to another aspect of the invention, the dietary supplement further comprises at least one thermogenic substance.

According to another aspect of the invention, the dietary supplement further comprises at least one satiety-promoting ingredient.

According to another aspect of the invention, the dietary supplement further comprises at least one antioxidant.

According to another aspect of the invention, the dietary supplement further comprises at least one prebiotic.

According to another aspect of the invention, the dietary supplement further comprises at least one probiotic.

According to another aspect of the invention, the dietary supplement further comprises at least one substance that decreases harmful cholesterol.

According to an aspect of the invention, there is provided a dietary supplement comprising *Smallanthus sonchifolius* and/or *Phyllostachys edulis*.

In aspects of the invention, extracts are obtained from the *Smallanthus sonchifolius* and/or *Phyllostachys edulis*.

The compositions of the invention may further comprise various *Smallanthus sonchifolius* and/or *Phyllostachys edulis* and extracts thereof, *Smallanthus sonchifolius* and/or *Phyllostachys edulis* combined with different amounts of biologically active small molecules or other therapeutic agents. The compositions of the present invention are particularly useful for promoting weight loss and/or the treatment of obesity.

The present invention is further directed to a weight loss composition useful for treatment of obesity, comprising as an active component an effective amount of at least one specific chlorogenic acid extracted from *Smallanthus sonchifolius* and/or *Phyllostachys edulis* and at least one substance for increasing energy.

The present invention is further directed to a weight loss composition useful for treatment of obesity, comprising as an active component an effective amount of at least one specific chlorogenic acid extracted from *Smallanthus sonchifolius* and/or *Phyllostachys edulis*, at least one substance for increasing energy and at least one antioxidant and/or at least one thermogenic substance and methods of using same.

The present invention is further directed to a weight loss composition useful for treatment of obesity, comprising as an active component an effective amount of at least one specific chlorogenic acid extracted from *Smallanthus sonchifolius* and/or *Phyllostachys edulis*, at least one substance for increasing energy, at least one antioxidant, at least one thermogenic substance and at least one prebiotic and/or probiotic and methods of using same.

The present invention is further directed to the weight loss composition for promoting weight loss in an individual in need thereof.

The present invention is further directed to methods for promoting weight loss by administering the weight loss composition to an individual in need thereof.

The present invention is further directed to the use of the weight loss composition in the preparation of a medicament for promoting weight loss in an individual in need thereof.

The present invention is further directed to methods for promoting weight loss by administering the combination of raw plants and standardized plant extracts in specific proportions.

Specific embodiments of the present invention are understood to comprise tubers and/or leaves of *Smallanthus sonchifolius* and/or *Phyllostachys edulis*; methods for preparing the same; and methods of preparing a dietary supplement to aid in body fat loss, promote lipolysis while affording protection against reactive oxygen species resulting from the β-oxidation of fats.

In another particular aspect of the present invention, there is provided a weight loss composition useful for treatment of obesity, comprising as an active component an effective amount of at least one specific chlorogenic acid extracted from *Smallanthus sonchifolius* and/or *Phyllostachys edulis*, and a physiologically acceptable carrier, at least one substance for increasing energy and/or at least one antioxidant and methods of using same.

In another embodiment of the present invention using *Smallanthus sonchifolius* and/or *Phyllostachys edulis* extracts, *Smallanthus sonchifolius* and/or *Phyllostachys edulis* extracts comprise about 1% to about 99% by weight of the composition. In a preferred embodiment, *Smallanthus sonchifolius* and/or *Phyllostachys edulis* extracts comprise about 10% to about 60% by weight of the composition. In a more preferred embodiment, *Smallanthus sonchifolius* and/or *Phyllostachys edulis* extracts comprise about 20% to about 50% by weight of the composition.

In an embodiment, the composition of the invention comprises *Smallanthus sonchifolius* and/or *Phyllostachys edulis* extract present in an amount of about 35% to about 40% by weight at least one substance for increasing energy and/or a thermogenic substance. Alternatively, the compositions of the invention can be administered sequentially or simultaneously in combination with at least one substance for increasing energy and/or a thermogenic substance.

In an embodiment, the composition of the invention comprises *Smallanthus sonchifolius* and/or *Phyllostachys edulis* extract having at least 1% chlorogenic acids by weight.

In an embodiment, the composition of the invention comprises *Smallanthus sonchifolius* and/or *Phyllostachys edulis* extract comprises about 20 to 90% chlorogenic acids by weight and about 5 to 40% 5-caffeoylquinic acid by weight.

In an embodiment, the composition of the invention comprises *Smallanthus sonchifolius* and/or *Phyllostachys edulis* extract comprises about 45% chlorogenic acids by weight and about 10% 5-caffeoylquinic acid by weight.

According to in an embodiment of the invention is a comestible composition comprising an extract of *Smallanthus sonchifolius* and/or *Phyllostachys edulis* and at least one substance for increasing energy wherein the extract of *Smallanthus sonchifolius* and/or *Phyllostachys edulis* comprises at least one specific chlorogenic acid, in an amount of at least 5% by weight. And according to in an embodiment of the invention the at least one specific chlorogenic acid is 5-caffeoylquinic acid.

In another aspect, the dietary supplement comprises phenolic acids selected from the group consisting of caffeic, chlorogenic, rosamarinic and ferrulic. More preferably, the compositions include at least 5% chlorogenic acids by weight of the composition; preferably including at least 10% chlorogenic acids by weight of the composition. Most preferably, the compositions are obtained from the extraction of *Smallanthus sonchifolius* and/or *Phyllostachys edulis* parts with an aqueous organic solution mixture, in particular a water and ethanol solution mixture, comprising small molecule compounds.

In another aspect, the dietary supplement comprises phenolic acids selected from the group consisting of caffeic, chlorogenic, rosamarinic and ferrulic. More preferably, the compositions include at least 5% chlorogenic acids by weight of the composition; preferably including at least 10% chlorogenic acids by weight of the composition. Most preferably, the compositions are obtained from the extraction of *Smallanthus sonchifolius* and/or *Phyllostachys edulis* plant parts with an aqueous organic solution mixture, in particular a water and ethanol solution mixture, comprising small molecule compounds.

In another aspect, the dietary supplement comprises about 100 to 700 mg *Smallanthus sonchifolius* and/or *Phyllostachys edulis* extract and about 100 to 700 mg caffeine.

In another aspect, the dietary supplement comprises about 150 to 400 mg *Smallanthus sonchifolius* and/or *Phyllostachys edulis* extract.

In another aspect, the dietary supplement comprises about 200 to 400 mg *Smallanthus sonchifolius* and/or *Phyllostachys edulis* extract and about 100 to 700 mg caffeine.

In another aspect, the dietary supplement comprises about 200 mg *Smallanthus sonchifolius* and/or *Phyllostachys edulis* extract and 200 mg caffeine.

In another aspect, the dietary supplement comprises about 200 mg *Smallanthus sonchifolius* extract and/or *Phyllostachys edulis* extract (containing about 45% by weight chlorogenic acids and about 5% by weight 5-caffeoylquinnic acid), about 200 mg of a substance for increasing energy in a capsule or tablet.

The *Smallanthus sonchifolius* or *Phyllostachys edulis* extracts obtained according to an aspect of the present invention have at least 1% by weight total phenolics, preferably at least 20% by weight total phenolics, and most preferably at least 40% by weight total phenolics.

One aspect of the invention comprises a composition containing about 100 to 700 mg *Smallanthus sonchifolius* or *Phyllostachys edulis* with 1-90% by weight chlorogenic acids.

One aspect of the invention comprises a composition comprising about 150 to 400 mg *Smallanthus sonchifolius* or *Phyllostachys edulis* extract containing about 5% to 70% by weight chlorogenic acids and about 100 to 700 mg caffeine.

In another aspect, the dietary supplement comprises about 200 mg *Smallanthus sonchifolius* or *Phyllostachys edulis* extract and about 100 to 700 mg caffeine.

In another aspect, the dietary supplement comprises about 200 mg *Smallanthus sonchifolius* or *Phyllostachys edulis* extract and 200 mg caffeine.

In another aspect, the extract of *Smallanthus sonchifolius* or *Phyllostachys edulis* comprises about 45 to 50% chlorogenic acids by weight and about 5 to 15% 5-caffeoylquinic acid by weight and the caffeine contains about 10% to 100% by weight 1,3,7-trimethylxanthine.

In another aspect, the *Smallanthus sonchifolius* or *Phyllostachys edulis* extract contains about 45% by weight chlorogenic acids and about 5% by weight 5-caffeoylquinnic acid.

Specific embodiments of the present invention are understood to function in the capacity of a dietary supplement to aid in body fat loss, lipolysis while affording protection against reactive oxygen species resulting from the β-oxidation of fats.

DETAILED DESCRIPTION OF THE EMBODIMENTS

As used herein, unless otherwise specified, the term "manage weight gain" includes, but is not limited to, treating, preventing or reducing weight gain, suppressing appetite.

As used herein, unless otherwise specified, the term "preventing," includes, but is not limited to, inhibition or the averting of symptoms associated with a particular disease or disorder.

As used herein, unless otherwise specified, the term "treating" refers to the administration of the composition after the onset of symptoms of the disease or disorder whereas "preventing" refers to the administration prior to the onset of the symptoms, particularly to patients at risk of the disease or disorder.

As used herein, unless otherwise specified, the term "obese" includes, but is not limited to, a person having a Body Mass Index (BMI) of greater than or equal to about 26.

As used herein, unless otherwise specified, the term "average weight" or "of average weight" includes, but is not limited to, a person having a Body Mass Index (BMI) of less than about 26.

As used herein, the term "thermogenic" refers to an ingredient, which increases energy expenditure, also known as metabolic rate. It is the process of burning stored body fat. The certain thermogenic ingredient may also have a property of inducing satiety.

The term "standardized" as used in the field of naturally derived nutritional products refers to the process for delivering a product with a specific minimum level of one or more plant constituents. Standardization represents the level of concentration of particularly desired elements from a plant source. Methods for standardizing plant substances are well known in the art. Furthermore, the measurement of particular plant constituents on which standardization is based is also well known in the art.

The term "about" when used as a modifier of a numerical range or amount designates an approximation of the range or the amount whereby minor deviations from the range or amount are within the scope of the invention. Such deviations are known in the art of manufacturing formulations having a number of different ingredients of varying weight and consistency.

The term "effective amount" shall be understood to mean an amount or quantity of the composition that is required to cause the metabolic effects described herein. This amount is readily determined by observation both before and after administration of the compositions described herein.

Unless specified otherwise, the term "% by weight" as used herein with reference to the standardized extract denotes the percent of the total weight of the extract contributed by the active component. This theoretical value can differ from the experimental value, because in practice, the extract typically may retain some of the water and/or other substances such as alcohols (e.g., ethanol) that may be used in preparing the final product. In addition, the chemical composition of the plant material from a particular plant may vary with, for example, the conditions under which the plant is grown (e.g., soil or climate).

The term "% by weight of the composition" as used herein shall be understood to denote the percentage of the dietary ingredients in the composition useful for supplementing the diet of an individual.

A particular compound or mixture of compounds can exhibit pharmacological activity over a readily ascertainable range of compositions and dosages. Therefore it will be understood that the percentages by weight recited throughout are meant to include such variations outside the stated percentages or percentage ranges as would be expected by one skilled in the art.

As used herein, unless otherwise specified, the term "physiologically acceptable carrier," includes, but is not limited to, a carrier medium that does not interfere with the effectiveness of the biological activity of any active ingredients, is chemically inert, and is not toxic to the consumer or patient to whom it is administered.

As used herein, unless otherwise specified, the term "pharmaceutically acceptable salts" refers to salts prepared from pharmaceutically acceptable non-toxic acids and bases, including inorganic and organic acids and bases.

It has now been shown that various raw botanicals and various extracts of raw botanical materials in the specific proportions reduce and control appetite; help induce feeling of satiety; promote and support weight loss; help reduce body mass index (BMI); help reduce waist and thigh measurements; increase metabolism; increase thermogenesis; and increase energy.

Phenolic compounds, widely distributed in food plants, act as primary antioxidants and thus may be beneficial for improving and/or preventing a number of chronic diseases. Phenolic compounds occur in nature as mixtures of esters, ethers, or free acids.

A major class of phenolic compounds are the hydroxycinnamic acids, which are found in almost every existing plant. Caffeic, ferulic and p-coumaric acids are trans-cinnamic acids that occur naturally in their free forms or as a family of mono or diesters with (−)-quinic acid, collectively known as chlorogenic acids. Chlorogenic acids are antioxidant components produced by plants in response to environmental stress conditions such as infections by microbial pathogens, mechanical wounding, and excessive UV or visible light levels. The main classes of chlorogenic acids found in nature are the caffeoylquinic acids, dicaffeoylquinic acids, and, less commonly, feruloylquinic acids, each group with at least three isomers. The term "chlorogenic acid" comprises 3-caffeoylquinic acid, 4-caffeoylquinic acid, 5-caffeoylquinic acid, 3,4-dicaffeoylquinic acid, 3,5-dicaffeoylquinic acid, 4,5-dicaffeoylquinic acid, 3-feruloylquinic acid, 4-feruloylquinic acid, 5-feruloylquinic acid, 3-feruloyl-4-caffeoylquinic acid and other structural isomeric chlorogenic acids such as 3-O-(3'-methylcaffeoyl)quinic acid, 5-O-caffeoyl-4-methylquinic acid and 3-O-caffeoyl-1-methylquinic acid or mixtures thereof.

Phenolic compounds are known to be anti-tumor agents. Chlorogenic acid has been shown to exert cancer preventive activities in animal models. Chlorogenic acid, an ester of caffeic acid and quinic acid, is an antioxidant in vitro and is suspected to be beneficial in preventing cardiovascular disease. Also, chlorogenic acid has shown to have a chemopreventative effect on rat stomach cancer, and to inhibit methylazoxymethanol induced large intestinal tumors in hamsters. Other beneficial properties such as hypoglycaemic, antiviral and hepatoprotective activities have been also attributed to chlorogenic acids in in vitro and in vivo and epidemiological studies.

Chlorogenic acid, the main phenolic acid in coffee, is able to protect the gastric mucosa against irritations, and, therefore, improves the digestibility of foods, beverages and medicaments. The improved digestibility is expressed through a much reduced systemic acid secretion (such as causes heartburn, etc.) which has been found to be directly dependent on an increased level of chlorogenic acid content in roasted coffee.

The chlorogenic acids of the present invention are not particularly limited, and, for instance, those commercially available, or those prepared from various plants in accordance with known methods can be used. Organically synthesized chlorogenic acid can be used in addition to or in place of the botanical extract.

It is now believed that certain dietary polyphenolic compounds, in addition to their antioxidant activities, may alter glucose metabolism. For instance, recent studies have linked heavy regular use of coffee to decreased risk for type 2 diabetes. The actions of caffeine seem unlikely to mediate this effect since it has been observed in those who use decaffeinated coffee. Caffeic acid, the hydrolytic product of chlorogenic acid, is known to have antidiabetic effects in streptozotocin-induced diabetic rats. Therefore, it is reasonable to expect that chlorogenic acids and/or caffeic acid in coffee may be responsible for these effects.

In vivo experiments studying the effects of chlorogenic acid have shown that it is able to arrest the proliferation of 3T3-preadipocyte cells in the G1 phase of development in a time- and dose-dependant manner. It is understood by the inventors that chlorogenic acid administration in vivo would translate into an inhibition of adipocytes differentiation and proliferation, resulting in a net reduction in adipose tissue.

Interestingly, in addition to the inhibitory effects of chlorogenic acid on preadipocyte proliferation, it has been suggested that chlorogenic acid decreases the intestinal rate of glucose absorption. Chlorogenic acid has also been shown to selectively inhibit hepatic glucose-6-phosphatase (G-6-P), the rate-limiting step in gluconeogenesis and decrease hepatic triglyceride levels in mice following 14 days of administration. Chlorogenic acid may also reduce glucose release from the liver which is often abnormally high in individuals with obesity, It has been shown that about 33% of orally administered chlorogenic acid is absorbed in the small intestine of humans and it is understood by the inventors that chlorogenic acid not only inhibits adipose tissue proliferation but it also inhibits of glucose absorption.

Chlorogenic acids, ferulic acid in particular, are also known to directly act on nitric oxide derived from the vascular endothelium. It is believed that this will support flow mediated vasodilation and delivery of nutrients via the systemic circulatory system.

According to an aspect of the present invention is the standardization of the total phenolics, chlorogenic acids, and the entire plant extract. The standardized extracts have better batch-to-batch consistency. They may also have higher amounts of at least one specific chlorogenic acid.

There is also a need for plant extracts that have been standardized to the presence of specific markers. Further there is a need for methods of preparing these extracts, as well as for compositions containing these extracts. There is also a need for methods to promote weight loss and/or the treatment of obesity and/or weight maintenance. According to an aspect of the present invention is the standardization of the total phenolics, chlorogenic acids, and the entire extract. The standardized extracts have better batch-to-batch consistency. They also have higher amounts of at least one specific chlorogenic acid. The inventive extracts can be standardized according to at least one assay. The extracts can be standardized by quantifying the concentration of total phenolics. The extracts can also be standardized by quantifying the concentration of specific chlorogenic acids.

The present invention further relates to an extract that has been standardized based on the concentration of individual specific chlorogenic acids. Specific chlorogenic acids may be assayed using High Performance Liquid Chromatography ("HPLC"). HPLC is known to those skilled in the art. Total phenolics can be assayed using the Folin-Ciocalteu ("FC") method and is known to those skilled in the art.

The extraction process may be carried out using methods known in the art, including but not limited to solvent extraction, percolation, vat extraction, or countercurrent extraction. The degree of comminutation of the plant material prior to the extraction process should provide sufficient particulate surface for the extraction solvent to contact the material. Extraction may be at ambient temperature or at elevated temperature. The resulting extract solution is then dried to substantially remove the solvent.

Chlorogenic acids may be extracted from the raw botanical material according to any known methods. The present invention further relates to a method of preparing an extract from leaves which comprises: treating a mass of plant material with a solvent suitable for extracting at least one chlorogenic acid to yield an extract solution; concentrating the extract solution to an extent necessary to provide a minimum desirable concentration of the active component for promoting weight loss, and; standardizing the extract to yield a known amount of at least one specific chlorogenic acid.

The extraction process according the present invention may be carried out using suitable solvents selected from water, and organic solvents with or without water. Suitable organic solvents include but are not limited to non-toxic aqueous or non-aqueous monohydric or polyhydric alcohols, hexane, methylene glycol, glycerin, and similar solvents known to those in the art. Other extraction methods such as use of super-critical $CO_2$ may also be used. Preferably an aqueous solvent having at least 10% volume/volume ("v/v") of an alcohol is used in the extraction, more preferably at least 30% v/v of an alcohol, and most preferably at least 50% v/v of an alcohol. The preferred alcohols are ethanol and methanol.

The concentration of total phenolics as well as certain specific phenolic markers is increased if the plant mass is freeze-dried after harvesting and before extraction or processing. In an aspect of the invention, the plant parts such as the bean, stems, leaves, or flowers are freeze-dried before extraction. Freeze-drying can be done immediately upon harvesting the plant. Or the harvested plant can immediately be frozen and then freeze-dried within at least 30 days.

The extracts obtained according to an aspect of the present invention have at least 1% by weight total phenolics, preferably at least 20% by weight total phenolics, and most preferably at least 40% by weight total phenolics.

Yacon (*Smallanthus sanchifolius*) is an Asteraceae from the Andean areas that grows in zone of not more than 3,000 meters of altitude and the culture of which has expanded to other latitudes. In Peru it is found especially in humid temperate areas in Andean slopes, in dry inter-Andean valleys, as well as in the coast. Both the tubercle and the leaves improve lipid profile as well as intestinal absorption of calcium. The tuberous roots of yacon accumulate almost 10%, based on the fresh weight, of inulin type fructooligosaccharides (FOSs), which are known as food ingredients with health benefits, the main saccharide being beta-1,2-oligofructane.

*Phyllostachys*, a genus of bamboo and more particularly, *Phyllostachys edulis*, is the largest of all temperate bamboos and produces edible shoots. The leaves of bamboo have been used in Asian countries as a food wrapping material to prevent food deterioration since ancient times. The leaves have been used in the clinical treatment of hypertension, arteriosclerosis, cardiovascular disease, and certain forms of cancer.

In particular, the present invention relates to a standardized extract of *Smallanthus sonchifolius* or *Phyllostachys edulis*, which comprises at least one specific chlorogenic acid, in an amount of at least 1% by weight based on the total weight of the extract. In a preferred embodiment the chlorogenic acid is in an amount of at least 5% by weight based on the total weight of the extract. In a more preferred embodiment, in an amount of at least 10% by weight. In a most preferred embodiment of the present invention, the total phenolics are present in an amount of at least 20% by weight.

The present invention further relates to a method of preparing an extract from *Smallanthus sonchifolius* or *Phyllostachys edulis*. This mass is subjected to an extraction process that is effective in concentrating at least one specific chlorogenic acid. The extract is then dried. The extract is then standardized according to the invention. The extract can further be combined with fillers, excipients, binders and the like to form a composition suitable for administration for the treatment of obesity.

In one specific method leaves of *Smallanthus sonchifolius* or *Phyllostachys edulis* are dried and comminuted and then extracted first with petroleum ether and next with hot water, until the extracts contain no more chlorogenic acid. The combined extracts are concentrated and precipitated with barium acetate. Then the filtrate is precisely neutralized with sulphuric acid, the excess barium being removed at the same time. The chlorogenic acid is separated from the neutral filtrate by means of lead acetate as a complex, which is washed with hot water and to which hydrogen sulphide is then added after suspension in hot water. After standing in a refrigerator for two to three days, the potassium-caffeine-chlorogenate complex separates from the concentrated filtrate. Caffeine is removed from the complex by chloroform and then the free chlorogenic acid is obtained by weak acidification.

In particular, in one embodiment of the invention, the extraction steps are as follows: a) *Smallanthus sonchifolius* is harvested during the early flowering season, when the amount of at least one specific phenolic marker is at its peak. b) The bean, stems, flowers, or leaves of the plant are immediately frozen to prevent fermentation, or are immediately freeze-dried. The frozen plant mass is freeze dried within one month of harvest. Freeze-drying is done at minimal heat. c) The freeze-dried material is pulverized to optimal particle size for percolation extraction. d) The pulverized material is then extracted and solid material is removed using the percolation method of extraction, in an ethanol/water solution wherein the ethanol is preferably 10% v/v, more preferably 30% v/v, and most preferably 50% v/v. e) The resulting extract is then dried and concentrated.

One aspect of the invention is a composition comprising *Smallanthus sonchifolius* or *Phyllostachys edulis* with a substance for increasing energy. In aspects, the substance for increasing energy is *Lepidium meyenii* and/or *Ptychopetalum olacoides*. *Lepidium meyenii* (Brassicaceae), known as Maca or Peruvian ginseng, is a perennial crop of Peru. For centuries, the Andean Indians have utilized maca as a food and for its pharmacological properties; for example to enhance fertility. As a food source, maca displays a high nutritional value and is rich in sugars, protein, starches and minerals. It has a fleshy, edible, tuberous root macca that has been domesticated for at least 2000 years in the Andean Mountains at an altitude more than 10,000 feet. Dried maca root is rich in amino acids, iodine, iron, and magnesium. Traditionally maca root has been used in the Andean region for its supposed aphrodisiac and/or fertility-enhancing properties and energy-increasing properties. Another species is *Lepidium peruvianum*.

*Muira puama* (*Ptychopetalum olacoides*) is a remedy for sexual impotence as wells as treating neuromuscular problems, rheumatism, influenza, cardiac and gastrointestinal asthenia and to prevent baldness. *Muira puama* also significantly inhibits anti-cholinesterase activity in vitro in a dose- and time-dependent manner in rat frontal cortex, hippocampus and striatum suggesting improvement in facilitate memory retrieval.

An established component of obesity is abnormal fat metabolism, specifically, the breakdown of fat, or lipolysis. Body fat, stored as triglycerides in adipose tissue, is hydrolyzed to free fatty acids and glycerol through the process of lipolysis. In fat cells (adipocytes) lipolysis is controlled by adrenergic signaling and signaling through adenosine receptors. Typically, stimulation of beta-adrenergic receptors increases lipolysis, whereas stimulation of adenosine A1 receptors inhibits lipolysis. The specific effects of stimulation or inhibition of either adrenergic or adenosine receptors depends on the cell- or tissue-type involved and the precise panel of receptors expressed and the downstream signaling connectivity.

Caffeine is a naturally occurring xanthine alkaloid found in some plants where it serves as a natural pesticide. In humans, however, it may have numerous beneficial effects, the most common of which uses caffeine as a supplement to the central nervous system. In this capacity, it is used as a stimulant and performance enhancer. Weight loss related to caffeine supplementation has been observed in obese women and may be, at least in part, due to increased lipolysis. Caffeine has additionally been shown to increase the basal metabolic rate.

While caffeine is structurally similar to adenosine, it binds to, but does not activate, adenosine receptors which are normally activated by adenosine to induce sleep. Thus, caffeine is a stimulant. By antagonizing certain adenosine receptors, caffeine has the effect of increasing levels of intracellular cyclic AMP (cAMP), an important signaling molecule involved in many metabolic processes including thermogenesis. Caffeine also increases cAMP levels by inhibiting phosphodiesterases which degrade cAMP. These actions of caffeine lead to an increase in the release of epinephrine and norepinephrine. Since epinephrine and norepinephrine use cAMP for signaling, increased levels of cAMP will increase adrenergic signaling and thereby inducing lipolysis.

In aspects, the caffeine comprises 1,3,7-trimethylxanthine. In another aspect 1,3-dimethylxanthine or 3,7-dimethylxanthine can be substituted for 1,3,7-trimethylxanthine.

Cirsimarin is a flavonoid extracted from several plants including *Microtea debilis* (Phytolaccaceae), an herb native to South America, which is thought to be involved in various pharmacological activities within the human body. Research suggests that cirsimarin may be a lipolytic agent due to its antagonist effects on both adenosine A1 and A2 receptors and inhibitory effects on the enzyme phosphodiesterase. Phosphodiesterases are the main enzymes involved in the hydrolysis of the signaling molecule, cAMP, and have inhibitory effects on lipolysis. It is known that adenosine receptor activation acts to inhibit lipolysis. Therefore it will be understood that by inhibiting phosphodiesterase and inhibiting adenosine receptors, the inhibition of lipolysis is removed and fat burning is promoted. Use of cirsimarin is contemplated because it stimulates lipolysis and promote weight loss by acting as a lipolytic agent due to its antagonism of adenosine receptors and its inhibition of phosphodiesterase.

Antioxidants are of great interest because they may help to protect the body against damage by reactive oxygen species (ROS). Studies have shown that free radicals present in the human organism cause oxidative damage to different molecules, such as lipids, proteins and nucleic acids, and thus are involved in the initiation phase of some degenerative illnesses. The ROS superoxide anion radical ($O_2^-$), hydrogen peroxide ($H_2O_2$), hypochlorous acid (HOCl) and hydroxyl radical ($HO^-$) have been implicated in the pathophysiology of various disorders; those antioxidant compounds, which are capable of neutralizing free radicals or ROS, may play a major role in the prevention of certain diseases, such as cancer, diabetes, cataracts, cerebral pathologies and rheumatoid arthritis.

Wolfberries, the common name for *Lycium barbarum*, also called Goji berries are a nutritionally rich fruit originally grown in Europe and now cultivated in China. *Lycium barbarum* contain all 8 essential amino acids, as well as 21 trace minerals and a variety of vitamins. In traditional Chinese medicine they have been used in for nearly 2,000 years. In support of these traditional properties assigned to *Lycium barbarum*, recent studies indicate that extracts from *Lycium barbarum* fruit possess a range of biological activities, including effects on aging, neuroprotection, antifatigue/endurance, increased metabolism, glucose control in diabetics, glaucoma, antioxidant properties, immunomodulation, antitumor activity, and cytoprotection. Its reddish-orange color is derived from a group of carotenoids, which make up only 0.03-0.5% of the dried fruit. The predominant carotenoid is zeaxanthin, comprising about one-third to one-half of the total carotenoids.

Other chemical constituents found in *Lycium barbarum* fruit include small molecules such as betaine, cerebroside, beta-sitosterol, p-coumaric acid, and various vitamins. Other minor components include glutamine; asparagine; stigmasterol; cholest-7-enol; campesterol; cholestanol; 24-methylene cholesterol; 28-isofucosterol; 24-methylcholesta-5,24-dienol; 24-ethylcholesta-5,24-dienol; 31-norcycloartanol; 31-norcycloartenol; cycloeucalenol; obtusifoliol; 4a,14a,24-trimethylcholesta-8'24-dienol; 4a-methylcholest-8-enol; 4-methylcholest-7-enol; 24-ethyllophenol; 4,24-methyllophenol; gramisterol; citrostadienol; 4a-methyl-24-ethylcholesta-7,24-dienol; lanost-8-enol; cycloartanol; lanosterol; b-amyrin; lupeol; 24-methylenelanost-8-enol; 24-methylenecycloartanol; taurine and -aminobutanoic acid.

It is understood that the polysaccharide extracts which contain six monosaccharides (Ara, Rha, Xyl, Man, Gal, and Glc), galacturonic acid, and 18 amino acids, and share a Glycan-O-Ser glycopeptide structure, provides benefits such as enhancing the immune system function, improving eyesight, protecting the liver, boosting sperm production, and improving circulation in an individual. The use of *Lycium barbarum* polysaccharides in the treatment of age-related oxidative stress in mice has been shown to improve the total antioxidant capacity as well as improved immune function. Furthermore, the same study also illustrated that the antioxidant activity of the wolfberries could be increased with co-treatment of vitamin C.

Acerola (*Malpighia emarginata*) one of the richest sources of vitamin C (L-ascorbic acid) an is also known as Barbados cherry, West Indian cherry, Puerto Rican cherry, Antilles cherry, cereso, cereza, cerisier, and semeruco is a fruit which has been used to treat dysentery, diarrhea, and liver disorders. Other ethnobotanical uses include as an astringent and for fever. Acerola is also used for preventing heart disease, "hardening of the arteries" (atherosclerosis), blood clots, and cancer.

Vitamin C, or L-ascorbic acid, is an essential nutrient required in small amounts in order to allow a range of essential metabolic reactions in animals and plants. Since the body does not make or store vitamin C, humans are required to ingest it in their daily diets. Ascorbic acid is a strong antioxidant and protects the body from oxidative stress, as well as acting as a coenzyme in necessary enzymatic reactions. As a strong antioxidant and anti-inflammatory molecule, ascorbic acid has been shown to protect against the common cold.

Cactus pear (*Opuntia ficus-indica*) fruit contains vitamin C and characteristic betalain pigments, the radical-scavenging properties and antioxidant activities. Consumption of cactus pear fruit positively affects the body's redox balance, decreases oxidative damage to lipids, and improves antioxidant status in healthy humans. Supplementation with vitamin C at a comparable dosage enhances overall antioxidant defense.

Blueberries are a group of flowering plants in the genus *Vaccinium*. The species are native to North America and eastern Asia and contain a high amount of anthocyanins, potent antioxidants.

Anthocyanins are the colorful flavonoids concentrated in brightly colored berries and fruit ("anthos" means "flower" and "cyan" means "blue") being most concentrated in bilberries, blueberries, cranberries, elderberries, purple grapes, red wine and hawthorn berries. Flavonoids have been reported to demonstrate their benefits in lowering oxidative stress and also have beneficial effects on cardiovascular and chronic inflammatory diseases.

Anthocyanin extracts are important for the health of the micro-blood vessel network and prevent blood platelet stickiness better than aspirin. Anthocyanins bind to and stabilize collagen and elastin; they stabilize the phospholipids of endothelial cells and increase synthesis of collagen and mucopolysaccharides, which give the arterial walls structural integrity.

Anthocyanins also inhibit the proliferation of human cancer cell lines in vitro, an effect attributed to their antioxidant activity. Anthocyanins induce the secretion of insulin from rodent pancreatic β-cells, the cells normally responsible for insulin secretion, which are the cells compromised in diabetes. Ingested anthocyanins have been shown to be detectable in the plasma and brain as intact molecules 10 minutes after ingestion by rats and to be excreted in the urine of both rats and humans. Antioxidant supplementation can reduce the markers of cellular damage. Therefore, supplemental with antioxidants should benefit any nutritional and exercise program.

Bilberries, *Vaccinium myrtillus* [Fam. Ericaceae], otherwise known as European blueberries, huckleberry or whortleberry are rich in anthocyanins. Bilberry has traditionally been used in herbal medicine as an astringent to help relieve diarrhea. Bilberry anthocyanin extracts are beneficial for the cardiovascular system have strong antiplatelet aggregating activity. Bilberry leaf constituents prevent the release and synthesis of pro-inflammatory compounds such as histamine, prostaglandins, and leukotrienes and bilberry anthocyanins also support the lymphatic system and prevent bacteria from adhering to the bladder wall. Bilberry extracts also exert potent protective action on LDL particles during copper-mediated oxidation.

Blueberries, *Vaccinium corybosum* and other and other blueberry species including *Vaccinium alaskensis*, *Vaccinium membranaceum* and *Vaccinium ovalifolium* [Fam. Ericaceae], are also rich anthocyanins.

Carotenoids are isoprenic compounds that are naturally occurring in plants. There are over 600 known carotenoids split into two classes: xanthophylls and carotenes. The 6 major carotenoids are: alpha-carotene, beta-carotene, lycopene (carotenes); beta-cryptoxanthin, zeaxanthin and lutein (xanthophylls). Zeaxanthin is found in many vegetables and fruits, particularly green leafy vegetables such as kale and spinach. Zeaxanthin is widely known as a nutrient for protecting ocular function. It has long been thought that carotenoid intake also reduces the risk of certain forms of cardiovascular disease, stroke, and cancer. Zeaxanthin and its stereoisomer lutein, may prevent cellular damage in these conditions by quenching singlet oxygen or neutralizing photosensitizers.

Açai berries (*Euterpe oleracea*) are a rich source of anthocyanin and polyphenolic compounds, essential fatty acids, and vitamins. Cyanidin-3-glucoside is the main anthocyanin (1,040 mg/L of açai berry juice), as well as 16 other polyphenolics at levels ranging from 4 to 212 mg/L. Total anthocyanin content is 3.2 mg/g freeze-dried açai berry samples on a dry weight basis where cyanidin-3-glucoside and cyanidin-3-rutinoside are the predominant anthocyanins. Resveratrol, albeit at very low levels, fatty acids, mainly oleic and palmitic acids can also be found in açai berry. Plasma antioxidant capacity of 2.3- and 3-fold is observed for açai juice and pulp after the consumption.

Gentian root and rhizome, *Gentiana lutea* L. [Fam. Gentianaceae], otherwise known as Bitter Root may have anti-inflammatory activity in addition to antioxidant activities such as hydroxyl radical scavenging.

Schisandrin B is a dibenzocyclooctadiene compound that is isolated from *Schisandrae chinensis*. Schisandrin has been used to enhance the detoxification of xenobiotics in the liver and assist in liver regeneration. Recent studies have shown that schisandrin can protect various organs from free-radical induced damage.

Furthermore, it is known that oxidized low density lipoprotein (LDL) is a key factor in the initiation of atherosclerosis, one of the pathological processes involved in cardiovascular and cerebrovascular disease. LDL expresses numerous adhesion molecules that appear to enhance the binding of monocytes to aortic endothelium, where they may become transformed into foam cells and initiate atherosclerosis. Research has shown that zeaxanthin can inhibit thickening of the walls of carotid arteries and LDL-induced migration of monocytes to human artery cell walls. It is believed that carotenoids for the ability to scavenge free radicals and inhibit lipid peroxidation in cardiovascular and cerebrovascular disease.

Phytosterols have cholesterol-lowering properties by reducing cholesterol absorption in intestines. The most abundant phytosterols (beta-sitosterol, campesterol, and stigmasterol) differ from cholesterol only in the identity of one side chain or the presence of an extra double bond. Cholesterol and phytosterol are very similar and the human body is not able to distinguish between them and therefore, phytosterols compete with cholesterol for absorption in the small intestine. A non-limiting list of phytosterols includes sitosterol, campesterol, sigmasterol, brassicasterol, sitostanol and campestanol.

Olive leaf comes from the olive tree (*Olea europaea*). Although olives and olive oil are used as foods, olive leaf is primarily used medicinally or as a tea. Olive leaf helps to maintain a healthy metabolism as well as lowering cholesterol and blood pressure in people with mild hypertension. According to an aspect of the invention, olive corresponding to about 500 mg to about 1 g dried plant is used. Preferably, olive corresponding to 450 mg dried plant is used.

Alfalfa (*Medicago sativa*) [Fam. Leguminosae] may have cholesterol-lowering effects. Alfalfa is also extremely rich in antioxidants, including one powerful antioxidant called tricin, and is a source of chlorophyll and carotene.

Oat bran, *Avena sativa* L. [Fam. Gramineae], is rich in protein, approximately 30%, and contains all the essential amino acids along with chlorophyll, flavonoids, lecithin and enzymes. This abundance of nutrients has made it popular for treating debility. It is also extremely rich in antioxidants, including polyphenols and one powerful antioxidant called tricin. It also contains beta-glucan, which has been shown to stimulate immune functions.

Angelica (*Angelica archangelica*) belongs to the family Umbelliferae. Angelica is said to be 'ginseng' for women and is recommended by many as a daily beauty tonic, to prevent hormonal imbalances and treat menstrual difficulties (Amenorrhea) and is recommended for the prevention of vascular disease. Angelica root is a source of bitters and aromatics that stimulate gastric and pancreatic secretion. Polysaccharide extract from the root Angelica has been studied for its liver protective effect in rodents and has been found to prevent liver toxicity caused by acetaminophen in mice without reducing the serum acetaminophen concentration. It also normalized enzyme activities and levels including alanine transferase (ALT), hepatic nitric oxide synthase (NOS) and glutathione in the liver.

Evening primrose oil [Gen. *Oenothera*] has been shown to decrease the risk of heart disease by lowering cholesterol and by decreasing the risk of blood clots (decreased platelet aggregation).

The flowers of *calendula*, *Calendula officinalis* [Fam. Asteraceae], contain high concentrations of colorful orange xanthophylls, carotenoids and other flavonoids that are powerful antioxidants and the flavonoid extract has been shown scientifically to be effective against inflammation, fever and to stimulate bile flow for aiding digestion and cleansing the liver.

Choline is a constituent of phosphatidylcholine (PC), which is a component of cell walls and membranes. It is involved in fat and cholesterol metabolism and transport. In this form, choline aids in fat metabolism and transport away from the liver.

Ginseng (American ginseng, Asian ginseng, Chinese ginseng, Korean red ginseng, *Panax ginseng*) appears to have antioxidant effects that may benefit patients with heart disorders. Studies suggest that ginseng also reduces oxidation of low-density lipoprotein (LDL or "bad") cholesterol and brain tissue. Several studies report that ginseng may boost the immune system, improve the effectiveness of antibiotics in people with acute bronchitis, and enhance the body's response to flu vaccines.

Pomegranate (*Punica granatum*) delivers approximately 40% of an adult's daily vitamin C requirement and is high in polyphenolic compounds. Juice of the pomegranate was effective in reducing heart disease risk factors, including LDL oxidation, macrophage oxidative status, and foam cell formation all of which are believed to be involved in atherosclerosis and cardiovascular disease. Consumption of pomegranate juice for two weeks was shown to reduce systolic blood pressure by inhibiting serum angiotensin-converting enzyme (ACE).

Inosine (also known as hypoxanthine riboside, hypoxanthosine, 2,3-diphosphoglycerate, 6-9 dihydro-9-B-D-ribofuranosyl-1 H-purin-6-one, 9-B-D-ribofuranosylhypoxanthine) and primarily used in the treatment for various forms of heart disease. Inosine monophosphate is a precursor for adenine, a nucleotide and purine base that reacts with ribose to form adenosine. Adenosine is a nucleoside that can be phosphorylated to produce adenosine monophosphate (AMP), the diphosphate (ADP), the triphosphate (ATP) and cyclic adenosine monophosphate (cAMP).

Gamma oryzanol is a mixture of ferulic acid esters of sterols and triterpene alcohols extracted from rice bran oil and other grain oils such as corn and barley. Ferulic acid compounds also are present in many foods, including oats, berries, citrus fruits, tomatoes, olives, and vegetables. Gamma oryzanol is an important antioxidant within plant cells.

Turmeric (*Curcuma longa*), a perennial herb and member of the Zingiberaceae (ginger) as is used as an anti-inflammatory and for the treatment of flatulence, jaundice, menstrual difficulties, hematuria, hemorrhage and colic. The active constituents of turmeric are the flavonoid curcumin (diferuloylmethane) and various volatile oils, including tumerone, atlantone, and zingiberone. Other constituents include sugars, proteins, and resins. There is about 0.3-5.4 percent of curcumin in raw turmeric. Water- and fat-soluble extracts of turmeric and its curcumin component exhibit strong antioxidant activity, comparable to vitamins C and E. Turmeric has been found to have a hepatoprotective characteristic similar to silymarin. Turmeric's hepatoprotective effect is primarily due to its antioxidant properties, as well as its ability to decrease the formation of pro-inflammatory cytokines.

Turmeric's protective effects on the cardiovascular system include lowering cholesterol and triglyceride levels, decreasing susceptibility of low density lipoprotein (LDL) to lipid peroxidation and inhibiting platelet aggregation. Turmeric extract's effect on cholesterol levels may be due to decreased cholesterol uptake in the intestines and increased conversion of cholesterol to bile acids in the liver. Inhibition of platelet aggregation by turmeric's constituents is thought to be via potentiation of prostacyclin synthesis and inhibition of thromboxane synthesis.

*Ficus carica* has antioxidant properties and is used to treat constipation, bronchitis, high cholesterol, eczema, psoriasis (chronic skin disease) and vitiligo (white skin patches).

Sunflower (*Helianthus annuus*) (Asteraceae) oil is rich in linoleic acid (omega-6), oleic acid (omega-9) and Vitamin E.

Bayberry (*Myrica cerifera*) (Myricaceae) stimulates lymphatic drainage and encourages the healing of mucus membranes. The primary chemical constituents of bayberry include essential oils, triterpenes (taraxerol, taraxaxerone, myricadol), flavonoids (myricitrin), phenols, starch, myrica wax (palmitic acid, stearic acid, myristic acid) lignin, albumin, gum, tannins and gallic acid. Bayberry is also been shown to alleviate arthritic pain.

Inulin (*Cichorium intybus*) is a type of naturally occurring fructose-containing oligosaccharide present in various fruits and vegetables such as onions, garlic, wheat, leeks, garlic, bananas, asparagus, and artichokes. Typically, inulin contains 2 to 150 fructose units which are linked by beta-(2-1) glycosidic bond with a terminal glucose. Inulin is resistant to digestion in the upper gastrointestinal tract and is fermented by the colonic bacteria, promoting intestinal bacteria and possibly acting as a mild laxative. In the colon, inulin is metabolized into short-chain fatty acids-acetate, propionate, and butyrate, lactic acids, and gases (e.g., hydrogen sulfide, carbon dioxide, and methane). Inulin is also reported to possess anti-tumor, antimicrobial, hypolipidemic, hypoglycemic, and antiosteoporotic effects and enhance mineral absorption and balance. Inulin from roots of chicory and Jerusalem artichokes are marketed as nutritional supplements and functional foods. Nutritionally, it is considered a form of soluble fibre. It is herein understood that inulin will act to benefit digestion by enhancing nutrient absorption, by promoting intestinal bacteria, and by mild laxative activity.

Inulin type fructooligosaccharides can be found in other plants. *Smallanthus sonchifolius* is also cultivated for its tubers, which are consumed mainly as a "fruit". In contrast with most edible roots, *Smallanthus sonchifolius* stores its carbohydrates in the form of beta-(2-1) fructooligosaccharides (FOS). FOS are sugars found naturally in many types of plants but never in concentrations as high as in *Smallanthus sonchifolius* roots. FOS are able to resist the hydrolysis of enzymes in the upper part of the human gastrointestinal tract. For this reason, they have a low caloric value for humans.

*Smallanthus sonchifolius* FOS are completely fermented in the colon by bacteria that form part of the intestinal microflora. These bacteria (especially of the genus *Bifidus* and *Lactobacillus*) improve the gastrointestinal function. In this regard, FOS functions as a prebiotic. Prebiotics are an alternative for probiotics or their cofactors. As non-digestible or low-digestible food ingredients that benefit the host organism by selectively stimulating the growth or activity of one or a limited number of probiotic bacteria in the colon. This role is played by fermentable carbohydrates, which are not digested or poorly digested in the small intestine and stimulate, preferentially, the growth of bifidobacteria and some Gram-positive bacteria, belonging to the probiotic bacteria administered to humans.

*Smallanthus sonchifolius* tubers show an important effect by producing a positive balance of calcium and magnesium, and thus obtaining a greater osseous mineral retention. FOS aid in digestion and prevent and control constipation. The sub-chronic use for 4 months of yacon root flour in male rats was well tolerated and did not show adverse effects or toxicity at a daily dose of 340 mg and 6800 mg FOS. Under these conditions, the triglyceride levels decreased, although no effects on glycemia were observed. It does not appear that the hypoglycemic effect of yacon is due to a lower intestinal absorption of glucose.

In one specific method yacon tubers are frozen (−20° C.) immediately after harvest. The frozen tubers are then cut into smaller parts and homogenized in a homogenizer for 30 s. Ten grams of yacon tubers are transferred into a 100 mL volumetric flask and filled with water. The extraction mixtures is ultrasonicated for 15 min and filtered. Three milliliters of the filtrates may be pipetted into 10 mL volumetric flasks and filled with methanol. Saccharide analysis of the tubers can be performed using techniques familiar to those skilled in the art. For example, extracts of yacon tubers can be analyzed for sugar content using high-performance thin-layer chromatography (HPTLC).

According to an aspect of the present invention is a syrup composition obtained from the tubers of *Smallanthus sonchifolius*. The syrup may be obtained from *Smallanthus sonchifolius* tubers according to methods known to those skilled in the art. For example, harvested tubers which contain about 40 to 70% FOS, 5 to 15% sucrose, 5 to 15% fructose and less than 5% glucose are juiced and filtered. The juice generally has an initial concentration of sugars in the range from 8 to 13° Brix. Removal of water via evaporation and concentration can increase the concentration to about 50 to 70° Brix.

In addition to prebiotics such as inulin and FOS, the use of probiotics is also contemplated. Probiotics are defined as selected, viable microbial dietary supplements beneficially affect the organism through their effects in the intestinal tract. Some strains of *Lactobacillus, Bifidobacterium* and *Saccharomyces*, for example have been promoted in food products because of their reputed health benefits.

The physiological effects related to probiotic bacteria include the reduction of gut pH, production of some digestive enzymes and vitamins, production of antibacterial substances, e.g., organic acids, bacteriocins, hydrogen peroxide, restoration of normal intestinal microflora after diarrhea, antibiotic therapy and radiotherapy, reduction of cholesterol level in the blood, stimulation of immune functions, suppression of bacterial infections and removal of carcinogens.

Psyllium is a water-soluble fiber derived from the husks of ripe seeds from *Plantago ovata*. Psyllium is widely used as a fiber supplement for the treatment of constipation. Psyllium husk is obtained by milling the seed of *P. ovata* to remove the hulls. Psyllium husk contains a high proportion of hemicellulose, composed of a xylan backbone linked with arabinose, rhamnose, and galacturonic acid units (arabinoxylans). The seed consists of 35-percent soluble and 65-percent insoluble polysaccharides (cellulose, hemicellulose, and lignin). Psyllium is classified as a mucilaginous fiber due to its powerful ability to form a gel in water. This ability comes from its role as the endosperm of the *P. ovata* seed, where it functions to retain water in order to prevent the seed from drying out. Psyllium also has hypocholesterolemic effects, although the exact mechanism by which psyllium husk brings about a reduction of cholesterol is not totally clear. Animal studies have shown psyllium increases the activity of cholesterol 7 alpha-hydroxylase (the rate-limiting enzyme in bile acid synthesis also referred to as cytochrome 7A [CYP7A]) more than twice that of cellulose or oat bran. Psyllium may also have an effect on appetite.

*Caralluma* is a cactus-like plant that grows abundantly in areas of Asia, the south Mediterranean, and parts of Africa. *Caralluma* is a cactus that has historical use as an appetite suppressant during times of famine in India and Africa. In India, the plant is boiled and eaten whole but elsewhere only the green follicles are consumed. The name of the plant varies between regions and in addition to *caralluma*, it is also known as: Ranshabar, Maked shenguli, and Shindala makad.

*Caralluma* is reported to have anti-inflammatory, anti-nociceptive, anti-hyperglycemic, anti-ulcer, cytoprotective and appetite suppressant properties. In addition to the anti-hyperglycemic and appetite suppressant properties, *caralluma* or an extract thereof may have other activities conducive to maintaining or reducing weight such as the blocking the activity of the fat synthesis enzyme, citrate lyase. The phytochemical constituents of *caralluma* include various glycosides (pregnane, flavone and megastigmane glycosides), bitter principles, saponins and various flavanoids.

There are a number of species of *caralluma* including but not limited to: *C. fimbriata, C. indica, C. attenuata, C. tuberculata, C. edulis, C. adscendens, C. stalagmifera, C. umbellata, C. penicillata, C. russeliana, C. retrospiciens, C. arabica* and *C. lasiantha*.

It is herein understood that inclusion of *Caralluma* or an extract thereof in a composition will support the maintenance or reduction of body weight in a subject by at least reducing appetite. It is further understood that *Caralluma* may further support the maintenance or reduction of body weight in a subject by antagonizing fat synthesis by blocking citrate lyase.

Cumin (*Cuminum cyminum*) is native from the eastern Mediterranean area to eastern India. It is used as a medicinal herb and in cooking throughout the Middle East, North Africa, South Asia, and parts of southern Europe. Evidence suggests that cumin may have antibacterial properties and has been used as a diuretic (increases urine production), dyspeptic (relieves indigestion), carminative (prevents gas), stimulant, astringent and eases digestion. According to an aspect of the invention, cumin corresponding to about 500 mg to about 1 g dried plant is used. Preferably, cumin corresponding to 384 mg dried plant is used.

Lady's mantle (*Alchemilla vulgaris*) is a perennial herb found in Europe, North America, and Asia that has been used medicinally since the Middle Ages. It helps maintain body weight. According to an aspect of the invention, lady's mantle corresponding to about 500 mg to about 1 g dried plant is used. Preferably, Lady's mantle corresponding to 690 mg dried plant is used.

Wild mint (*Mentha longifolia*) is known for the treatment of colic, menstrual disorders, indigestion, flatulence, pulmonary infection and congestion, headache, fever, cough, colds and urinary tract infections. It also stimulates the flow of bile to the stomach and relaxes the digestive tract muscles. According to an aspect of the invention, wild mint corresponding to about 500 mg to about 1 g dried plant is used. Preferably, wild mint corresponding to 324 mg dried plant is used.

A water extract of the common white kidney bean (*Phaseolus vulgaris*) inhibits digestive enzyme alpha-amylase in vitro. Alpha-amylase, secreted in saliva and by the pancreas, is responsible for breaking down starch to simple sugars that are absorbed in the small intestine. Blocking this digestive enzyme may prevent the digestion of complex carbohydrates, allowing them to pass through the digestive system. The end result of blocking alpha-amylase would logically be a decrease in the number of calories absorbed, potentially promoting weight loss.

Chromium, an essential trace mineral and cofactor to insulin, enhances insulin activity and has been the subject of studies assessing its effects in carbohydrate, protein, and lipid metabolism. Reported effects include an increase in lean body mass, a decrease in percentage body fat, and an increase in the basal metabolic rate. Chromium picolinate is an organic compound of trivalent chromium and picolinic acid, a naturally occurring derivative of tryptophan Calcium carbonate is a colorless or white crystalline compound, $CaCO_3$, occurring naturally as chalk, limestone, marble, and other forms and used in a wide variety of manufactured products including dentifrices and medicines.

Although the present invention is not to be limited by any theoretical explanation, it is believed that increased calcium intake has a significant effect on body weight and body fat.

Studies show a consistent effect of higher calcium intakes, expressed as lower body fat and/or body weight, and reduced weight gain at midlife. Specifically, calcium may assist in weight loss, weight management, regulation of metabolism, and the breakdown of fat. Studies show that increasing dietary calcium speeds up weight and fat loss. In a comparison trial, both the diets, either high in calcium or low in calcium, produced significant weight and fat loss. Weight and fat loss with respect to the high dairy diet were approximately 2-fold higher (p<0.01), and loss of lean body mass was markedly reduced (p<0.001) compared with the low dairy diet. This study purports to show that employing calcium-rich foods in isocaloric diets reduced adiposity and improved metabolic profiles in obese African Americans. Additionally, calcium carbonate facilitates the prevention and treatment of calcium deficiencies, and thereby facilitates bone formations and maintenance.

Furthermore, it is known that that an isocaloric substitution of yogurt (diary) for other foods can significantly reduce central adiposity during energy restriction and therefore augment fat loss. This was purportedly shown by the use of control subjects (400-500 mg Ca/day), or yogurt diet (1100 mg Ca/day) with the dairy macronutritents controlled to the United States average values. After 12 weeks, fat loss was markedly increased in the yogurt group, and mean tissue loss was also increased in the yogurt group by 31%. Compared to the control group, an 81% increase in trunk fat loss was also purported to be seen in the yogurt group, this resulted in decrease in waist diameter in yogurt group. It has been shown that calcium and dairy supplementation accelerated fat and weight loss during a 24 week controlled study. Subjects on high-dairy diet (1200-1300 mg Ca/day) reportedly lost 70% more weight than those on the standard diet of 400-500 mg Ca/day and subjects on the calcium enriched, but non-dairy diet lost on 26% more weight than those on the standard diet. Therefore, this study purports to show that calcium supplementation significantly increases weight loss and that calcium supplementation from diary sources exerts a substantially greater effect of the weight and fat loss.

It is believed that a high calcium diet in the form of dairy products or as calcium carbonate may be useful in inducing the loss of adipose tissues via stimulating lipolysis, inhibiting lipogenesis, and increasing the expression of uncoupling protein 2 in white adipose tissue.

Vitamin D is a steroid hormone, known to have an important role in regulating body levels of calcium and phosphorus, and in mineralization of bone. Vitamin D is particularly important for the absorption of calcium from the stomach and for the functioning of calcium in the body. Thus, vitamin D is particularly important for strong bones and teeth. Vitamin D is also known as cholecalciferol, which is generated in the skin of animals when light energy is absorbed by a precursor molecule 7-dehydrocholesterol. Cholecalciferol is used as a dietary supplement to treat and/or prevent low levels of vitamin D in the body. Although the present invention is not to be limited by any theoretical explanation, it is believed that vitamin D is highly involved in mineral metabolism, as well as bone growth and function. It has been shown that vitamin D effectively facilitates intestinal absorption of calcium, and stimulates absorption of phosphate and magnesium ions. In the absence of vitamin D, dietary calcium may not be absorbed efficiently. Vitamin D stimulates the expression of a number of proteins involved in transporting calcium from the lumen of the intestine, across the epithelial cells and into blood.

Vitamin B3 (Niacin) also known as or nicotinic acid is one of several water-soluble B-family vitamins. Niacin is often consumed as a nutritional dietary supplement in the form of a multi-vitamin/mineral complex to improve general health. As a supplement in itself, niacin has long been successfully used to improve blood lipid profiles. Xanthinol nicotinate is one of several forms of Niacin (vitamin B3) and is considered the most potent form of Niacin. Xanthinol nicotinate is classified as a vasodilator. In patients with peripheral arterial obliterative disease, xanthinol nicotinate was found to have anti-platelet and thrombolytic actions accompanied by an increase in the release of NO. Xanthinol nicotinate may also have the effects of enhancing cellular metabolism and increasing oxygen supply which may be the mechanism of improvements in both short- and long-term memory.

Compositions of the present invention may be formulated for administration to any suitable subject to promote weight loss. In a preferred embodiment, the subject is a mammal and even more preferably, the mammal is a human.

The administration may be by any conventional route such as oral, rectal, or nasal. Thus the composition may be a tablet, capsule, suspension, emulsion, solution, suppository or spray. The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). Non-limiting examples of binders include starch, and sugars such as sucrose, glucose and dextrose. Non-limiting examples of disintegrators include corn and potato starch, methylcellulose, agar, and bentonite. Non-limiting examples of coloring agents include any of the approved certified water-soluble FD&C dyes and mixtures of the same.

Tablets provided in accordance with the present invention may be uncoated or they may be coated by known techniques. In a preferred embodiment, the pharmaceutical composition may take the form of a capsule or powder to be dissolved in a liquid for oral consumption. Preparations for oral administration may be suitably formulated to give controlled release of the active compound.

Formulations for oral use include tablets or capsules which contain the active ingredients mixed optionally with pharmaceutically acceptable inert excipients.

Such excipients include for example: inert diluents such as calcium carbonate, sodium chloride, lactose, calcium phosphate, sodium phosphate, dicalcium phosphate, calcium sulfate, mannitol, sorbitol, and the like, etc.; granulating and disintegrating agents, for example, potato starch, alginic acid, etc.; binding agents, for example, starch, gelatin or acacia, etc.; and lubricating agents for example, magnesium stearate, stearic acid or talc. Non-limiting examples of lubricants include talc, starch, paraffin, stearic acid, magnesium stearate, and calcium stearate.

Other pharmaceutically acceptable excipients include colorants, flavoring agents, plasticizers, humectants, etc. In certain embodiments, the active ingredient(s) may be delivered in a soft or hard gel capsule by mixing the active ingredient with water or oil such as peanut oil, or olive oil and enclosing the resulting formulation in a capsule. Suitable colorants include dyes that are generally suitable for food, drug and cosmetic applications, i.e., those known as F.D.&C. dyes.

The extracts of the present invention can be processed in the usual way for the preparation of the compositions, including but not limited to tablets, controlled-release products, capsules, caplets, solutions, and the like. The composition can also be formulated as confections including but not limited to gums, lozenges, troches and the like. One preferred composition is as a tablet containing between 50-300 mg of the extract or the raw plant material, and more preferably containing 100-200 mg of the extract or the raw plant material.

The preparation may be in liquid form, for example, solutions, syrups or suspensions, or may be presented as a powdered product for reconstitution with water, beverage or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

The composition can be formulated to provide a homogenous mixture, or the composition can be formulated so that the components are non-homogenous.

The dosage may also be administered as an oral liquid dosage form by suspending the active ingredients or extracts thereof in an aqueous solution in admixture with a dispersing or wetting agent, suspending agent and one or more preservatives. Suitable dispersing or wetting agents are, for example, naturally occurring phosphatides, for example, lecithin, or condensation products of ethylene oxide, fatty acids, long chain aliphatic acids, or a partial ester derived from fatty acids and a hexitol or hexitol anhydrides, for example, polyoxyethylene stearate, polyoxyethylene sorbitol monooleate, polyoxyethylene sorbitan monooleate, etc. Suitable suspending agents are, for example, sodium carboxymethylcellulose, methylcellulose, sodium alginate, etc.

The solubility the acids in water can be improved by providing them in the form of a pharmaceutically acceptable salt, and their physiological effectiveness can be enhanced. Examples of a basic substance used for forming such a salt include inorganic bases such as alkali metal or alkaline earth metal hydroxides, for example, such as lithium hydroxide, sodium hydroxide, potassium hydroxide, magnesium hydroxide and calcium hydroxide; and ammonium hydroxide; and organic bases, such as basic amino acids such as arginine, lysine, histidine and ornithine; and monoethanolamine, diethanolamine and triethanolamine, with the alkali metal or alkaline earth metal hydroxides being particularly preferred. The agents according to the present invention may be formulated either by preparing such a salt and adding the salt to other components, or by separately adding a salt-forming component and a component to be formed into a salt to other components to react them in the formulation system.

For buccal administration, the compositions may take the form of tablets or lozenges formulated in conventional manner. Lozenges will typically be shaped solids containing the extract in a candy or glycerinated base.

Alternatively, the active ingredients of the present invention may be delivered over an extended time period by delaying disintegration and absorption in the gastrointestinal tract to provide a sustained release effect. A time delay material such as glyceral monostearate or glycerol distearate may be employed for this purpose. Extended release formulations that may be employed to deliver the active ingredients of the invention are well known in the art.

If the composition is water-soluble, then it may be formulated in an appropriate buffer, for example, phosphate buffered saline or other physiologically compatible solutions. Alternatively, if the resulting composition has poor solubility in aqueous solvents, then it may be formulated with a non-ionic surfactant such as Tween or polyethylene glycol. Thus, the compositions and their physiologically acceptable solvates may be formulated for administration by inhalation or insufflation (either through the mouth or the nose), oral, buccal, parenteral, or rectal administration.

For rectal applications, suitable formulations for compositions according to the present invention include suppositories (emulsion or suspension type), and rectal gelatin capsules (solution or suspensions). In a typical suppository formulation, the active ingredients are combined with an appropriate pharmaceutically acceptable suppository base such as cocoa butter, esterified acids, glycerinated gelatin, and various water soluble or dispersable bases like polyethylene glycols and polyoxyethylene glycols and polyoxyethylene sorbitan fatty acid esters.

The compositions may, if desired, be presented in a pack or dispenser device which may comprise one or more unit dosage forms comprising the active ingredient. The pack may for example comprise metal or plastic foil, such as a blister pack. The pack or dispenser device may be accompanied by instructions for administration.

The composition can also be formulated as a confection such as a gum, lozenge, troche, and the like. Components that may be incorporated into a confection include but are not limited to sweeteners, coloring agents, flavoring agents, preservatives, diluents, emulsifying agents, excipients, and the like.

Suitable sweeteners may be readily selected by those skilled in the art, and the amount of sweetener to be determined by taste. The sweetener may be naturally occurring or synthetic, and may be nutritive or non-nutritive. Examples of such sweeteners include, but are not limited to, the saccharides, sugar alcohols such as alcohol and mannitol, water-soluble artificial sweeteners such as soluble saccharine salts, and dipeptide-based sweeteners such as L-aspartyl-L-phenylalanine methyl ester. Flavorings may include natural or artificial flavors such as mint oils, citrus oils, and the like.

The composition may be prepared as a gum using conventional means. The "gum base" may be one a number of types of compositions, typically prepared by heating and blending various ingredients, e.g., natural gums, synthetic resins, waxes, and the like. Waxes, including natural and synthetic waxes, petroleum waxes, paraffin waxes and microcrystalline waxes may also be incorporated into the gum base.

A preferred composition is a controlled-release formulation. Controlled-release formulations may employ alginates, microcrystalline cellulose, cellulose ethers, vegetable gums, and polymer complexes to sustain the extract in the system. Physical means such as coating, microencapsulation, and embedding in complex matrices may be employed for this purpose. A preferred physical means is microencapsulation.

Other techniques known in the art can also be used to produce a controlled release composition. The controlled release composition yields an immediate release of effective dosage, and a sustained release such as to yield an effective dosage duration ranging from 3-6 hours, preferably 3.5 to 4.5 hours.

In addition to the foregoing, compositions of the present invention include formulations further comprising additional active ingredients and/or inactive ingredients, including solvents, diluents, suspension aids, thickening or emulsifying agents, sweeteners, flavorings, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and which may also be suitable for use in formulations of the present invention.

In accordance with an aspect of the present invention, the extract can be included in the preparation of pharmaceutical compositions containing a sufficient concentration of the extract to achieve a desirable pharmaceutical effect within an acceptable dosage regimen. All the compositions can be standardized for total phenolics, chlorogenic acids and specific chlorogenic acids by varying the amount of standardized extract added during the compounding process.

The present invention provides a method for promoting weight loss. The composition may be provided 1 to 7 times daily in conjunction with proper diet and physical exercise. The exact dosage and dosage forms will vary according to the individual to be treated and will depend on such factors such as requirements of the individual, the severity of the disorder or condition being treated and the age and health of the person being treated, as well as use of other medications and herbal remedies. The determination of optimum dosages can be made for a particular patient by one skilled in the art. An example of an effective amount of the *Smallanthus sonchifolius* extract of the present invention is between about 5 to 5000 mg, and especially between about 10 to 500 mg, a day per adult (weight: 60 kg).

The magnitude of the therapeutic dose of an active ingredient in the acute or chronic management of a disorder or condition will vary with the severity of the disorder or condition to be treated and the route of administration. The dose, and perhaps the dose frequency, may vary according to age, body weight, response, and the past medical history of the consumer or patient. Suitable dosing regimens can be readily selected by those skilled in the art with due consideration of such factors.

Except insofar as any conventional carrier medium is incompatible with the ingredients of the invention, such as by producing any undesirable effect or otherwise interacting in a deleterious manner with any other ingredient(s) of the formulation, its use is contemplated to be within the scope of this invention.

EXAMPLES

Example 1

Example 1. It has now been shown that a dietary supplement prepared according to the following specification in caplet form promote and support weight loss; help reduce body mass index (BMI); help reduce waist measurements; increase metabolism; increase thermogenesis and increase energy.

| Dietary Ingredient Name | Actives % |
| --- | --- |
| caffeine | |
| *Smallanthus sonchifolius* extract, leaves | |
|    Chlorogenic acids | 45 |
|    5-caffeoylquinic acid | 10 |
| *Phyllostachys edulis* extract | |
| *Lepidium meyenii* | |

Example 2

A serving of the dietary supplement was prepared and comprises the following ingredients in powder form.

| Dietary Ingredient Name | Actives % |
| --- | --- |
| Anhydrous caffeine | |
| *Smallanthus sonchifolius* extract | |
|    Chlorogenic acids | 45 |
|    5-caffeoylquinic acid | 10 |
| Goji Extract (*Lycium barbarum*) | |
|    std to polysaccaharides | 3 |
| Acerola Extract (*Malpighia glabra*), fruit | |
| Zeaxanthin | |
| Blueberry Powder (*Vaccinium corymbosum*), fruit | |
| Pomegranate powder (*Punica granatum*), fruit | |
| Bilberry Extract (*Vaccinium myrtillus*), fruit | |
| Vitamin C 95% | |
|    std to Ascorbic Acid | 95 |
| Vitamin D3 100,000 IU/g | |

Example 3

A serving of the dietary supplement was prepared and comprises the following ingredients in powder form.

| Dietary Ingredient Name |
| --- |
| Psyllium powder (*Plantago ovata*), seed |
| *Smallanthus sonchifolius* extract |
| Oat Bran (*Avena sativa*) |
| Inulin (*Cichorium intybus*), root |

Example 4

A serving of the dietary supplement was prepared and comprises the following ingredients in caplet form.

| Dietary Ingredient Name | Active Stan. (%) |
| --- | --- |
| *Smallanthus sonchifolius* extract, | |
|    Chlorogenic acids | 45 |
|    5-caffeoylquinic acid | 10 |
| Goji extract (*Lycium barbarum*), fruit | |
|    Std to Polysaccharides | 3 |
| Acerola concentrate 4-5:1 (*Malpighia glabra*), fruit | |
|    Supplying bioflavonoids | |
| Vitamin C - Ascorbic acid | |
|    Std to Ascorbic acid | 95 |
| Blueberry powder (*Vaccinium corymbosum*), fruit | |
|    Supplying flavonoids | |
| Pomegranate powder (*Punica granatum*), fruit & seed | |
| Bilberry extract 4:1 (*Vaccinium myrtillus*), fruit | |
|    Supplying Anthocyanins | |
| Zeaxanthin | |
|    Supplying Zeaxanthin | 5 |
| Vitamin D3 (as cholecalciferol) beadlets - 1,000,000 IU | |

Example 5

A serving of the dietary supplement was prepared and comprises the following ingredients in powder form.

| Dietary Ingredient Name | Active Stan. (%) |
|---|---|
| Caffeine Anhydrous | |
| Smallanthus sonchifolius extract | |
| inosine | |
| L-Histidine | |
| Muira Puama Powder(Ptychopetalum Uncinatum/Olacoides), Bark | |
| Taurine | |
| L-glutamine | |
| L-ornithine hcl | |
| Gamma -Oryzanol | |
| Phytosterol Complex | |
| Total phytosterols | 90 |
| Beta-sitosterol | 40 |
| Campesterol | 20 |
| Stigmasterol | 14 |
| Buffalo Herb (Medicago sativa) | |
| Mycozyme (Fungal Amylase 1000 Units/Gram) | |
| DL-Malic Acid | |

Example 6

A serving of the dietary supplement was prepared and comprises the following ingredients in caplet form.

| Dietary Ingredient Name | Active Stan. (%) |
|---|---|
| Vitamin C - Ascorbic acid | |
| Std to Ascorbic acid | 94 |
| Natural caffeine extract (Coffea arabica) 50:1, bean/seed | |
| Std to Caffeine | 90 |
| Smallanthus sonchifolius extract | |
| Std to Chlorogenic acid | 45 |
| Std to 5-coffeoylquinic acid | 10 |
| Std to Caffeine | 2 |
| White kidney powder (Phaseolus vulgaris), bean/seed | |
| Acerola juice powder 5:1 (Malpighia glabria), fruit | |
| Asian ginseng powder (Panax ginseng), root | |
| Opuntia ficus-indica powder, leaf | |
| Schizandra chinensis powder, fruit | |
| Turmeric powder (Curcuma longa), root | |
| Vitamin H | |
| Biotin | 1 |
| Choline bitartrate - encapsulated | |
| Choline bitartrate | 88 |
| Goji extract 6:1 (Lychium barbarum), fruit | |
| Std to Polysaccharide | 3 |
| Pomegranate powder (Punica granatum), fruit & seed (whole fruit) | |
| Vitamin B3 - nicotinamide | |
| Vitamin B6 - Pyridoxine HCl granular | |
| Pyridoxine HCl | 96 |
| Pyridoxine | 82 |
| Vitamin D3 (as cholecalciferol) beadlets - 1,000,000 IU | |
| Chromium picolinate (Chromax) | |
| Chromium | 12.18 |

Example 7

A serving of the dietary supplement was prepared and comprises the following ingredients in capsule form.

| Dietary Ingredient Name | Active Stan. (%) |
|---|---|
| Calcium carbonate | |
| Calcium | 39 |
| Natural caffeine dry concentrate extract (Coffea arabica), seed/bean | |
| Std to Caffeine | 90 |
| Smallanthus sonchifolius extract, | |
| Chlorogenic acid | 45 |
| 5-caffeoylquinic acid | 10 |
| Caffeine | 2 |
| White kidney bean powder (Phaseolus vulgaris), bean | |
| Isoleucine | |
| Threonine | |
| Inositol | |
| Angelica archangelica powder, root | |
| Bayberry powder (Myrica cerifera), bark | |
| Bilberry powder (Vaccinium myrtillus), fruit | |
| Gentiana lutea powder, root | |
| Niacin (as nicotinic acid) | |
| Calendula officinalis powder, aerial parts/herb top | |
| Ficus carica powder, fruit | |
| Sunflower oil powder (Helianthus annuus), seed | |
| L-glutamic acid hydrochloride | |
| Evening primrose oil (Oenothera biennis), seed | |
| Std to Gamma-linoleic | 10 |
| Folic acid | |
| Folic acid | 10 |
| Vitamin D3 - 1,000,000 IU/g (liquid) | |
| Chromium picolinate | |
| Chromium | 12.68 |

Example 8

A comestible composition is prepared according to following proportions: 198 mg of an extract of Smallanthus sonchifolius and 2 mg of vitamin C.

Example 9

A serving of the dietary supplement was prepared and comprises Smallanthus sonchifolius, Lepidium meyenii and caffeine in syrup form providing between 0.07 g and 0.21 g FOS/kg/day.

In the foregoing specification, the invention has been described with specific embodiments thereof; however, it will be evident that various modifications and changes may be made thereto without departing from the broader spirit and scope of the invention.

We claim:
1. A comestible composition, comprising an effective amount of:
   Smallanthus sonchifolius;
   at least one substance for increasing energy selected from the group consisting of Lepidium meyenii, Ptychopetalum olacoides, and a mixture thereof;

at least one lipolytic agent selected from the group consisting of caffeine, an extract of *Microtea debilis* and a mixture thereof; and at least one member selected from the group consisting of *Gentiana lutea* and extracts thereof.

2. The composition of claim 1, comprising said extract of *Microtea debilis*, wherein the extract of *Microtea debilis* comprises cirsimarin.

3. The composition of claim 2, further comprising at least one antioxidant.

4. The composition of claim 3, wherein the at least one antioxidant is selected from the group consisting of *Lycium barbarum, Malpighia glabra, Vaccinium corymbosum, Punica granatum, Euterpe oleracea, Vaccinium myrtillus, Lycium barbarum* extract, *Malpighia glabra* extract, *Vaccinium corymbosum* extract, *Punica granatum* extract, *Euterpe oleracea* extract, *Vaccinium myrtillus* extract, zeaxanthin, and vitamin C.

5. The composition of claim 4, wherein the antioxidant is an extract of *Lycium barbarum* comprising about 3% polysaccharides by weight.

6. The composition of claim 3, further comprising at least one phytosterol.

7. The composition of claim 6, wherein the at least one phytosterol is selected from the group consisting of beta-sitosterol, campesterol and stigmasterol.

8. The composition of claim 1, wherein the *Smallanthus sonchifolius* comprises extracts obtained from the leaves or tubers.

9. The composition of claim 8, comprising extracts obtained from the tubers.

10. The composition of claim 1, further comprising at least one of *Medicago sativa, Ptychopetalum olacoides, Phaseolus vulgaris, Panax ginseng, Opuntia ficus, Schizandra chinensis, Curcuma longa, Microtea debilis, Medicago sativa* extract, *Ptychopetalum olacoides* extract, *Phaseolus vulgaris* extract, *Panax ginseng* extract, *Opuntia ficus* extract, *Schizandra chinensis* extract, *Curcuma longa* extract, *Microtea debilis* extract, *Chromium picolinate*, vitamin B3, vitamin B6, vitamin H and vitamin D3.

11. The composition of claim 1, further comprising at least one member selected from the group consisting of *Angelica archangelica, Myrica cerifera, Ficus carica, Helianthus annuus, Oenothera biennis, Calendula officinalis*, and extracts thereof.

12. The composition of claim 1, further comprising at least one of isoleucine, threonine, L-histidine, L-glutamine, L-ornithine, gamma oryzanol, inosine, inositol, L-glutamic acid, niacin, calcium carbonate, choline bitartrate and folic acid.

13. The composition of claim 1, further comprising *Cuminum cyminum, Alchemilla vulgaris, Olea europaea* and *Mentha longifolia*.

14. The composition of claim 1, further comprising *Phyllostachys edulis*.

15. The composition of claim 14, wherein the *Phyllostachys edulis* is an extract of *Phyllostachys edulis* having at least 1% chlorogenic acids by weight.

16. The composition of claim 15, wherein the extract of *Phyllostachys edulis* comprises about 20 to 90% chlorogenic acids by weight and about 5 to 40% 5-caffeoylquinic acid by weight.

17. The composition of claim 16, wherein the extract of *Phyllostachys edulis* comprises about 45% chlorogenic acids by weight and about 10% 5-caffeoylquinic acid by weight.

18. The composition of claim 14, wherein the at least one substance for increasing energy comprises is *Ptychopetalum olacoides*.

19. A method for at least one of promoting and supporting weight loss; reducing body mass index; reducing waist measurements; increasing metabolism; increasing thermogenesis; and increasing energy, the method comprising administering to a subject an effective amount of the composition according to claim 1.

20. A method for at least one of promoting and supporting weight loss; reducing body mass index; reducing waist measurements; increasing metabolism; increasing thermogenesis; and increasing energy, the method comprising administering to a subject an effective amount of the composition according to claim 18.

* * * * *

UNITED STATES PATENT AND TRADEMARK OFFICE
CERTIFICATE OF CORRECTION

PATENT NO. : 8,372,447 B2
APPLICATION NO. : 12/849076
DATED : February 12, 2013
INVENTOR(S) : John Doherty et al.

It is certified that error appears in the above-identified patent and that said Letters Patent is hereby corrected as shown below:

COLUMN 1:

Line 62, "loss" should read --lose--.

COLUMN 4:

Line 11, "comprises" should read --comprising--;
Line 15, "comprises" should read --comprising--;
Line 17, "According to in" should read --In--; and
Line 23, "in" should be deleted.

COLUMN 8:

Line 2, "of" should be deleted; and
Line 40, "comminutation" should read --comminution--.

COLUMN 9:

Line 13, "Asteraceae" should be italicized;
Line 14, "zone" should read --zones--; and
Line 21, "inulin type" should read --inulin-type--.

COLUMN 10:

Line 17, "Brassicaceae," should be italicized; and
Line 37, "facilitate" should read --facilitating--.

Signed and Sealed this
Twenty-eighth Day of May, 2013

Teresa Stanek Rea
*Acting Director of the United States Patent and Trademark Office*

COLUMN 11:

Line 11, "Phytolaccaceae," should be italicized.

COLUMN 12:

Line 8, "provides" should read --provide--.

COLUMN 13:

Line 8, "Ericaceae" should be italicized;
Line 13, "have" should read --and have--;
Line 23, "Eri-" should be italicized;
Line 24, "caceae" should be italicized;
Line 51, "Genti-" should be italicized; and
Line 52, "anaceae" should be italicized.

COLUMN 14:

Line 4, "for" should read --have--;
Line 23, "olive" should read --olive leaf--;
Line 25, "olive" should read --olive leaf--;
Line 26, "Leguminosae" should be italicized;
Line 30, "Gramineae" should be italicized;
Line 39, "Umbelliferae" should be italicized; and
Line 57, "Asteraceae" should be italicized.

COLUMN 15:

Line 22, "furanosyl-1 H" should read --furanosyl-1H--;
Line 37, "Zingiteraceae" should be italicized;
Line 64, "Asteraceae" should be italicized; and
Line 66, "Myricaseae" should be italicized.

COLUMN 16:

Line 22, "are" should read --is--; and
Line 23, "fibre." should read --fiber.--.

COLUMN 17:

Line 20, "affect" should read --affecting--; and
Line 66, "the" (first occurrence) should be deleted.

CERTIFICATE OF CORRECTION (continued)
U.S. Pat. No. 8,372,447 B2

COLUMN 18:

Line 60, "tryptophan" should read --tryptophan.--.

COLUMN 21:

Line 34, "solubility" should read --solubility of--.

COLUMN 22:

Line 40, "one" should read --one of--.

COLUMN 23:

Line 47, "promote and support" should read --promotes and supports-- and
        "help" should read --helps--;
    Line 48, "help" should read --helps--; and
    Line 49, "increase" (all occurrences) should read --increases--.

COLUMN 27:

Line 39, "Chromium picolinate" should not be italicized.

COLUMN 28:

Line 11, "*europaea*and" should read --*europaea* and--.